United States Patent
Shimano et al.

(10) Patent No.: US 9,126,934 B2
(45) Date of Patent: Sep. 8, 2015

(54) PROCESS FOR PRODUCING 4-CARBONYLOXYQUINOLINE DERIVATIVES

(75) Inventors: Shizuo Shimano, Ageo (JP); Akinori Morikawa, Kamisu (JP); Kenichi Yamamoto, Kamisu (JP); Hiroki Hotta, Saitama (JP); Kazumi Yamamoto, Kamakura (JP); Nozomu Nakanishi, Yokohama (JP); Nobuto Minowa, Yokohama (JP)

(73) Assignees: NIPPON KAYAKU CO., LTD., Tokyo (JP); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 13/885,783

(22) PCT Filed: Nov. 16, 2011

(86) PCT No.: PCT/JP2011/076370
§ 371 (c)(1),
(2), (4) Date: May 16, 2013

(87) PCT Pub. No.: WO2012/067136
PCT Pub. Date: May 24, 2013

(65) Prior Publication Data
US 2013/0245271 A1    Sep. 19, 2013

(30) Foreign Application Priority Data
Nov. 19, 2010   (JP) ................. 2010-258856

(51) Int. Cl.
C07D 215/38   (2006.01)
C07D 215/20   (2006.01)
C07D 215/14   (2006.01)

(52) U.S. Cl.
CPC .......... C07D 215/20 (2013.01); C07D 215/14 (2013.01)
USPC ......................... 546/159; 546/162

(58) Field of Classification Search
CPC ........................... C07D 215/20; C07D 215/14
USPC ................... 546/159, 162; 504/247
See application file for complete search history.

(56) References Cited

U.S. PATENT DOCUMENTS 7,880,006 B2 *  2/2011   Yamamoto et al. .......... 546/159
8,367,833 B2 *  2/2013   Kato et al. .................... 546/159

FOREIGN PATENT DOCUMENTS

| JP | 52-10237 | | 1/1977 |
|---|---|---|---|
| JP | 62-63541 | * | 3/1987 |
| JP | 2008-110953 | | 5/2008 |
| TW | 201014528 | | 4/2010 |
| WO | 2006/013896 | | 2/2006 |
| WO | 2007/088978 | | 8/2007 |
| WO | 2010/007964 | * | 1/2010 |

OTHER PUBLICATIONS

Watarai, Interfacial Nanochemistry: Molecular Science and Engineering at liquid-liquid Interfaces, Springer Science & Business media, Mar. 30, 2006, p. 64.*
International Preliminary Report on Patentability issued Jun. 12, 2013 and English translation of Written Opinion of the International Searching Authority issued Dec. 13, 2011 for PCT/JP2011/076370.
International Search Report issued Dec. 13, 2011 in International (PCT) Application No. PCT/JP2011/076370.
"$4^{th}$ edition Jikken Kagaku Koza 27 Seibutsu Yuki", edited by The Chemical Society of Japan, May 5, 1991, pp. 251-260, cited in the International Search Report.
Extended European Search Report issued Mar. 31, 2014 in corresponding European Application No. 11 84 1056.
Illi, "Phase Transfer Catalyzed Acylation", Tetrahedron Letters, 1979, vol. 26, No. 26, pp. 2431-2432.
Houlihan et al., "Phase transfer catalysis in the tert-butyloxycarbonylation of alcohols, phenols, enols, and thiols with di-tert-butyl dicarbonate",Canadian Journal of Chemistry, 1985, vol. 63, No. 1, pp. 153-162.
Khalil et al., "Phase-transfer catalyzed acylation of 5(3)-hydroxy-3(5)-substituted-1H-p3rrazoles", Indian Journal of Chemistry, 2006, vol. 45, No. 1, pp. 2485-2490.
Chinese Office Action dated Jun. 4, 2014 issued in corresponding Chinese Application No. 201180055571.X (with English translation).
Taiwan Office Action dated May 26, 2015, issued in Taiwan Patent Application No. 100141814 (with English translation).
European Office Action dated Jun. 17, 2015 issued in European Patent Application No. 11841056.2.

* cited by examiner

*Primary Examiner* — D M Seaman
(74) *Attorney, Agent, or Firm* — Wenderoth, Lind & Ponack, L.L.P.

(57) ABSTRACT

An objective of the present invention is to provide a process for producing 4-carbonyl oxyquinoline derivatives useful as agricultural and horticultural pesticides and fungicides. The objective can be attained by a process for producing 4-carbonyl oxyquinoline derivatives represented by general formula (1), the process including reacting a quinolone derivative with a halogenated compound or an acid anhydride in the presence of a phase transfer catalyst and a base.

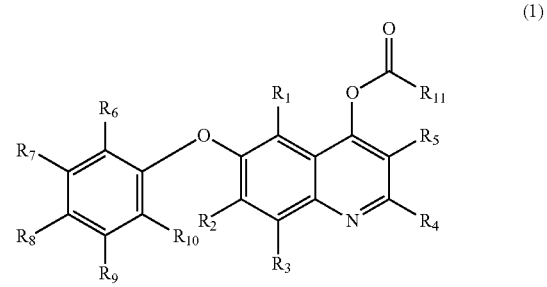

(1)

4 Claims, No Drawings

PROCESS FOR PRODUCING 4-CARBONYLOXYQUINOLINE DERIVATIVES

CROSS-REFERENCE TO RELATED APPLICATION

This patent application is based upon and claims the benefit of priority from the prior Japanese Patent Application No. 258856/2010, filed on Nov. 19, 2010, the entire contents of which are incorporated herein by reference.

BACKGROUND OF THE INVENTION

1. Field of the invention

The present invention relates to a process for producing 4-carbonyloxyquinoline derivatives useful as agricultural chemicals.

2. Background Art

4-Carbonyloxyquinoline derivatives are disclosed as compounds that are useful as agricultural and horticultural insecticides or agricultural and horticultural fungicides in WO2006/013896 (patent document 1), Japanese Patent Application Laid-Open Publication No. 110953/2008 (patent document 2), and WO2007/088978 (patent document 3). These 4-carbonyloxyquinoline derivatives are compounds having high insecticidal activity against *Lepidoptera, Hemiptera, Coleoptera, Acari, Hymenoptera, Orthoptera, Diptera, Order Thysanoptera*, and plant parasitic nematodes. Further, the 4-carbonyloxyquinoline derivatives are known as agricultural and horticultural insecticides fungicides that are effective against various plant pathogenic fungi, for example, exhibit fungicidal effects against *Sphaerotheca fuliginea, Puccinia recondita f.* sp. *tritici, Blumeria graminis, Alternaria solani, Venturia inaequalis, Monilinia fructicola* and *Glomerella cingulata*. A process for producing the 4-carbonyloxyquinoline derivatives is disclosed in WO2010/007964 (patent document 4).

This patent document discloses a process for producing 4-carbonyloxyquinoline derivatives that includes reacting a quinolone derivative with a halogenated compound or an acid anhydride in the presence of a base. Bases such as sodium hydride and sodium-t-butoxide used in this process are highly reactive and hygroscopically decomposable and thus are difficult to handle. Accordingly, close regulation of charging equivalent is necessary to avoid the decomposition of the product. In addition, bases such as sodium hydride and sodium-t-butoxide are expensive. Therefore, a further improvement as a commercial industrial process is demanded. Further, when bases such as sodium hydride and sodium-t-butoxide are used, a large amount of high-boiling amide solvents such as dimethyl acetamide should be used as the reaction solvent. Further, in the isolation of the 4-carbonyloxyquinoline derivatives, a larger amount of water should be added. Accordingly, there is a possibility that the operation efficiency is lowered in the isolation of the product. Contamination of a large amount of the amide solvent into waste water causes a large load on waste water, and the solvent should be recovered from the aqueous solution. However, due to high boiling point, a large amount of energy that is sometimes disadvantageous in industrial production, is necessary for the recovery of the solvent.

Accordingly, it can be said that the development of a more advantageous industrial process for producing 4-carbonyloxyquinoline derivatives that have been found to be useful as insecticidal compounds and fungicidal compounds has been desired.

PRIOR ART REFERENCES

Patent Documents

[Patent document 1] WO2006/013896
[Patent document 2] Japanese Patent Application Laid-Open Publication No. 110953/2008
[Patent document 3] WO2007/088978
[Patent document 4] WO2010/007964

SUMMARY OF THE INVENTION

The present inventors have found that the use of a phase transfer catalyst in a reaction between a quinolone derivative and a halogenated compound or an acid anhydride in a process for producing 4-carbonyloxyquinoline derivatives makes it possible to use inexpensive and easy-to-handle bases and, by virtue of this, the production process has no need to closely regulate the equivalent of the base charged and can use reaction solvents easily removable by evaporation, and can reduce a load on waste water, that is, is industrially advantageous, and, at the same time, can realize a high yield. The present invention has been made based on these finding.

Accordingly, an object of the present invention is to provide a process for producing 4-carbonyloxyquinoline derivatives that is industrially advantageous.

According to the present invention, there is provided a process for producing 4-carbonyloxyquinoline derivatives represented by general formula (1) that is industrially advantageous. Specifically, according to the present invention, there is provided a process for producing a 4-carbonyloxyquinoline derivative represented by general formula (1):

[Chemical formula 1]

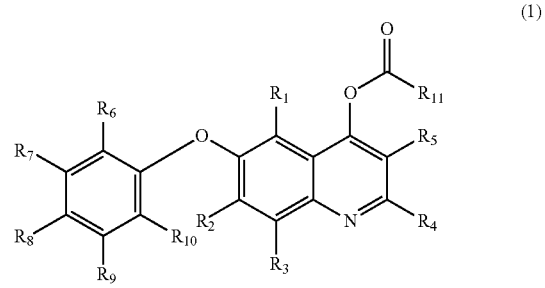

wherein
$R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom, $R_4$ and $R_5$ each independently represent a hydrogen atom or $C_{1-4}$ alkyl optionally substituted by a halogen atom(s), provided that $R_4$ and $R_5$ do not simultaneously represent a hydrogen atom, or $R_4$ and $R_5$ together represent —(CH$_2$)m— wherein m is 3 or 4, and $R_6$, $R_7$, $R_8$, $R_9$, and $R_{10}$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s), or any two adjacent substituents of $R_6$, $R_7$, $R_8$, $R_9$, and $R_{10}$ together represent —O—(CH$_2$)n-O— optionally substituted by one or more halogen atoms, wherein n is 1 or 2 and $R_{11}$ represents $C_{1-8}$ alkyl optionally substituted by a halogen atom(s); $C_{3-6}$ cyclic alkyl optionally substituted by a halogen atom(s); $C_{2-4}$ alkenyl optionally substituted by a halogen atom(s); $OR_{12}$ wherein $R_{12}$ represents $C_{1-8}$ alkyl optionally substituted by a halogen atom(s), $C_{3-6}$ cyclic alkyl optionally substituted by a halogen atom(s), or $C_{2-4}$ alkenyl optionally substituted by a halogen atom(s); $SR_{13}$ wherein $R_{13}$ represents $C_{1-8}$ alkyl optionally substituted by a halogen atom(s), $C_{3-6}$ cyclic alkyl optionally substituted by a halogen atom(s), or $C_{2-4}$ alkenyl optionally substituted by a halogen atom(s), the process comprising reacting a quinolone derivative represented by general formula (2):

[Chemical formula 2]

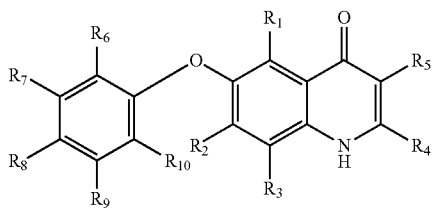

(2)

wherein $R_1$, $R_2$, $R_3$, $R_4$, $R_5$, $R_6$, $R_7$, $R_8$, $R_9$, and $R_{10}$ are as defined in formula (1), with a halogenated compound represented by general formula (3):

[Chemical formula 3]

$R_{11}COX$ (3)

wherein $R_{11}$ is as defined in formula (1); and X represents any one of fluorine, chlorine, bromine, and iodine, or an acid anhydride represented by general formula (4):

[Chemical formula 4]

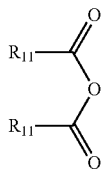

(4)

wherein $R_{11}$ is as defined in formula (1), in the presence of a phase transfer catalyst and a base.

According to the present invention, inexpensive and easy-to-handle bases are usable, and, by virtue of this, the production process has no need to closely regulate the equivalent of the base charged and can use reaction solvents easily removable by evaporation, and can reduce a load on waste water, that is, is industrially advantageous, and, at the same time, can realize a high yield.

DETAILED DESCRIPTION OF THE INVENTION

Definition of Substituents in General Formulae

The term "halogen atom" as used herein means a fluorine, chlorine, bromine, or iodine atom, preferably a fluorine, chlorine, or bromine atom, more preferably a chlorine or fluorine atom.

The term "cyclic alkyl" as used herein means that the alkyl group contains at least one cyclic structure. Examples of cyclic alkyl include cycloalkyl; and alkyl groups substituted by one or more cycloalkyls. They may be further substituted by one or more alkyls.

$C_{1-4}$ alkyl represented by $R_1$, $R_2$, and $R_3$ may be of a straight chain or branched chain type. Examples thereof include methyl, ethyl, propyl, i-propyl, n-butyl, i-butyl, s-butyl, and t-butyl. Preferably, the $C_{1-4}$ alkyl is straight chain $C_{1-4}$ alkyl, and examples thereof include methyl, ethyl, propyl, and n-butyl. Methyl or ethyl is more preferred.

$C_{1-4}$ alkyl represented by $R_1$, $R_2$, and $R_3$ is optionally substituted by a halogen atom(s). Examples of $C_{1-4}$ alkyl that is substituted by a halogen atom(s) and is represented by $R_1$, $R_2$, and $R_3$ include chloromethyl, trichloromethyl, trifluoromethyl, (1- or 2-)chloroethyl, 2,2,2-trifluoroethyl, 1,1,2,2-tetrafluoroethyl, and pentafluoroethyl. Trifluoromethyl is preferred.

$C_{1-4}$ alkyl represented by $R_1$, $R_2$, and $R_3$ is optionally substituted by $C_{1-4}$ alkoxy. Examples of $C_{1-4}$ alkyl that is substituted by $C_{1-4}$ alkoxy and is represented by $R_1$, $R_2$, and $R_3$ include methoxymethyl.

$C_{1-4}$ alkoxy represented by $R_1$, $R_2$, and $R_3$ may be of straight chain or branched chain type, and examples thereof include methoxy, ethoxy, n-propyloxy, i-propyloxy, n-butyloxy, i-butyloxy, s-butyloxy, and t-butyloxy. Preferably, the $C_{1-4}$ alkoxy is straight chain $C_{1-4}$ alkoxy, and examples thereof include methoxy, ethoxy, n-propyloxy, and n-butyloxy. Methoxy or ethoxy is more preferred.

$C_{1-4}$ alkoxy represented by $R_1$, $R_2$, and $R_3$ is optionally substituted by a halogen atom(s). Examples of $C_{1-4}$ alkoxy that is substituted by a halogen atom(s) and is represented by $R_1$, $R_2$, and $R_3$ include trifluoromethoxy, trichloromethoxy, difluoromethoxy, dichloromethoxy, 2,2,2-trifluoroethoxy, 2,2,2-trichloroethoxy, 1,1,2,2-tetrafluoroethoxy, pentafluoroethoxy, and pentachloroethoxy.

In a preferred embodiment of the present invention, $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom. More preferably, any one of $R_1$, $R_2$, and $R_3$ represents methyl, trifluoromethyl, or methoxy with the other two substituents representing a hydrogen atom. Particularly preferably, any one of $R_1$ and $R_2$ represents methyl, trifluoromethyl, or methoxy, the other substituent represents a hydrogen atom, and $R_3$ represents a hydrogen atom.

$C_{1-4}$ alkyl represented by $R_4$ and $R_5$ may be of straight chain or branched chain type, and examples thereof include methyl, ethyl, propyl, i-propyl, n-butyl, i-butyl, s-butyl, and t-butyl. Methyl or ethyl is preferred.

$C_{1-4}$ alkyl represented by $R_4$ and $R_5$ is optionally substituted by a halogen atom(s). Examples of $C_{1-4}$ alkyl that is substituted by a halogen atom(s) and is represented by $R_4$ and $R_5$ include chloromethyl, trichloromethyl, trifluoromethyl, (1- or 2-)chloroethyl, 2,2,2-trifluoroethyl, 1,1,2,2-tetrafluoroethyl, and pentafluoroethyl.

$C_{1-4}$ alkyl represented by $R_4$ and $R_5$ is optionally substituted by $C_{1-4}$ alkoxy optionally substituted by a halogen atom(s). Examples of $C_{1-4}$ alkyl that is substituted by $C_{1-4}$ alkoxy optionally substituted by a halogen atom(s) and is represented by $R_4$ and $R_5$ include 2-trifluoromethoxyethyl.

In a preferred embodiment of the present invention, $R_4$ and $R_5$ each independently represent a hydrogen atom or $C_{1-4}$ alkyl optionally substituted by a halogen atom(s), provided that $R_4$ and $R_5$ do not simultaneously represent a hydrogen atom. In a more preferred embodiment, $R_4$ and $R_5$ each independently represent $C_{1-4}$ alkyl optionally substituted by a halogen atom(s). Preferably, the $C_{1-4}$ alkyl in these embodiments is straight chain $C_{1-4}$ alkyl.

In a more preferred embodiment of the present invention, $R_4$ represents —$CH_2$—$R_{14}$; $R_5$ represents $R_{14}$; and $R_{14}$ represents $C_{1-3}$ alkyl. $C_{1-3}$ alkyl represented by $R_{14}$ may be of straight chain or branched chain type. The $C_{1-3}$ alkyl is preferably straight chain $C_{1-3}$ alkyl, more preferably methyl.

$C_{1-8}$ alkyl represented by $R_6$, $R_7$, $R_8$, $R_9$, and $R_{10}$ may be of straight chain or branched chain type, and examples thereof include methyl, ethyl, propyl, i-propyl, n-butyl, i-butyl, s-butyl, t-butyl, n-pentyl, (2- or 3-methyl)pentyl, (2,3-, 2,4-, or 3,4-dimethyl)butyl, 2,3,4-trimethylpropyl, n-heptyl, and n-octyl. Methyl or ethyl is preferred.

$C_{1-8}$ alkyl represented by $R_6$, $R_7$, $R_8$, $R_9$, and $R_{10}$ is optionally substituted by a halogen atom(s). Examples of $C_{1-8}$ alkyl that is substituted by a halogen atom(s) and is represented by $R_6$, $R_7$, $R_8$, $R_9$, and $R_{10}$ include chloromethyl, trichloromethyl, trifluoromethyl, (1- or 2-)chloroethyl, 2,2,2-trifluoroethyl, 1,1,2,2-tetrafluoroethyl, and pentafluoroethyl. Trifluoromethyl or pentafluoroethyl is preferred.

$C_{1-8}$ alkyl represented by $R_6$, $R_7$, $R_8$, $R_9$, and $R_{10}$ is optionally substituted by $C_{1-4}$ alkoxy optionally substituted by a halogen atom(s). Examples of $C_{1-8}$ alkyl that is substituted by $C_{1-4}$ alkoxy optionally substituted by a halogen atom(s) and is represented by $R_6$, $R_7$, $R_8$, $R_9$, and $R_{10}$ include 2-trifluoromethoxyethyl.

$C_{1-8}$ alkoxy represented by $R_6$, $R_7$, $R_8$, $R_9$, and $R_{10}$ may be of straight chain or branched chain type, and examples thereof include methoxy, ethoxy, n-propyloxy, i-propyloxy, n-butyloxy, i-butyloxy, s-butyloxy, t-butyloxy, n-pentyloxy, (2- or 3-methyl)butyloxy, 2,3-dimethylpropyloxy, n-hexyloxy, (2,3 or 4-methyl)pentyloxy, (2,3-, 2,4-, or 3,4-dimethyl)butyloxy, 2,3,4-trimethylpropyloxy, n-heptyloxy, and n-octyloxy. Methoxy or ethoxy is preferred.

$C_{1-8}$ alkoxy represented by $R_6$, $R_7$, $R_8$, $R_9$, and $R_{10}$ is optionally substituted by a halogen atom(s). Examples of $C_{1-8}$ alkoxy that is substituted by a halogen atom(s) and is represented by $R_6$, $R_7$, $R_8$, $R_9$, and $R_{10}$ include trifluoromethoxy, trichloromethoxy, difluoromethoxy, dichloromethoxy, 2,2,2-trifluoroethoxy, 2,2,2-trichloroethoxy, 1,1,2,2-tetrafluoroethoxy, pentafluoroethoxy, and pentachloroethoxy. Trifluoromethoxy, difluoromethoxy, or 1,1,2,2-tetrafluoroethoxy is preferred, and trifluoromethoxy or 1,1,2,2-tetrafluoroethoxy is more preferred.

$C_{1-8}$ alkylthio represented by $R_6$, $R_7$, $R_8$, $R_9$, and $R_{10}$ may be of straight chain or branched chain type, and examples thereof include methylthio, ethylthio, n-propylthio, i-propylthio, n-butylthio, i-butylthio, s-butylthio, t-butylthio, n-pentylthio, (2- or 3-methyl)butylthio, 2,3-dimethylpropylthio, n-hexylthio, (2,3 or 4-methyl)pentylthio, (2,3-, 2,4-, or 3,4-dimethyl)butylthio, 2,3,4-trimethylpropylthio, n-heptylthio, and n-octylthio. Methylthio or ethylthio is preferred.

$C_{1-8}$ alkylthio represented by $R_6$, $R_7$, $R_8$, $R_9$, and $R_{10}$ is optionally substituted by a halogen atom(s). Examples of $C_{1-8}$ alkylthio that is substituted by a halogen atom(s) and is represented by $R_6$, $R_7$, $R_8$, $R_9$, and $R_{10}$ include trifluoromethylthio, trichloromethylthio, difluoromethylthio, dichloromethylthio, trifluoroethylthio, trichloroethylthio, tetrafluoroethylthio, tetrachloroethylthio, pentafluoroethylthio, pentachloroethylthio, heptafluoro-n-propylthio, and heptafluoro-i-propylthio. Preferred is trifluoromethylthio, trichloromethylthio, difluoromethylthio, dichloromethylthio, trifluoroethylthio, trichloroethylthio, tetrafluoroethylthio, tetrachloroethylthio, heptafluoro-n-propylthio, or heptafluoro-i-propylthio. More preferred is trifluoromethylthio, difluoromethylthio, heptafluoro-n-propylthio, or heptafluoro-i-propylthio.

$C_{2-4}$ alkenyloxy represented by $R_6$, $R_7$, $R_8$, $R_9$, and $R_{10}$ may be of straight chain or branched chain type, and examples thereof include vinyloxy, (1- or 2-)propenyloxy, (1-, 2-, or 3-)butenyloxy, 1-methylvinyloxy, 1-methyl-1-propenyloxy, and 2-methyl-1-propenyloxy. The $C_{2-4}$ alkenyloxy is preferably straight chain $C_{2-4}$ alkenyloxy, and examples thereof include vinyloxy, (1- or 2-)propenyloxy, and (1-, 2-, or 3-)butenyloxy.

$C_{2-4}$ alkenyloxy represented by $R_6$, $R_7$, $R_8$, $R_9$, and $R_{10}$ is optionally substituted by a halogen atom(s). Examples of $C_{2-4}$ alkenyloxy that is substituted by a halogen atom(s) and is represented by $R_6$, $R_7$, $R_8$, $R_9$, and $R_{10}$ include 2-fluorovinyloxy, 2-chlorovinyloxy, 2,2-difluorovinyloxy, 2,2-dichlorovinyloxy, and 3,3-dichloro(1- or 2-)propenyloxy.

$C_{2-4}$ alkenyloxy represented by $R_6$, $R_7$, $R_8$, $R_9$, and $R_{10}$ is optionally substituted by $C_{1-4}$ alkoxy optionally substituted by a halogen atom(s). Examples of $C_{2-4}$ alkenyloxy that is substituted by $C_{1-4}$ alkoxy optionally substituted by a halogen atom(s) and is represented by $R_6$, $R_7$, $R_8$, $R_9$, and $R_{10}$ include 2-trifluoromethoxyvinyloxy.

$C_{2-4}$ alkenylthio represented by $R_6$, $R_7$, $R_8$, $R_9$, and $R_{10}$ may be of straight chain or branched chain type, and examples thereof include vinylthio, (1- or 2-)propenylthio, (1-, 2-, or 3-)butenylthio, 1-methylvinylthio, 1-methyl-1-propenylthio, and 2-methyl-1-propenylthio. The $C_{2-4}$ alkenylthio is preferably straight chain $C_{2-4}$ alkenylthio, and examples thereof include vinylthio, (1- or 2-)propenylthio, and (1-, 2-, or 3-)butenylthio.

$C_{2-4}$ alkenylthio represented by $R_6$, $R_7$, $R_8$, $R_9$, and $R_{10}$ is optionally substituted by a halogen atom(s). Examples of $C_{2-4}$ alkenylthio that is substituted by a halogen atom(s) and is represented by $R_6$, $R_7$, $R_8$, $R_9$, and $R_{10}$ include 2-fluorovinylthio, 2-chlorovinylthio, 2,2-difluorovinylthio, and 2,2-dichlorovinylthio.

$C_{2-4}$ alkenylthio represented by $R_6$, $R_7$, $R_8$, $R_9$, and $R_{10}$ is optionally substituted by $C_{1-4}$ alkoxy optionally substituted by a halogen atom(s). Examples of $C_{2-4}$ alkenylthio that is substituted by $C_{1-4}$ alkoxy optionally substituted by a halogen atom(s) and is represented by $R_6$, $R_7$, $R_8$, $R_9$, and $R_{10}$ include 2-trifluoromethoxyvinylthio.

$C_{2-4}$ alkynyloxy represented by $R_6$, $R_7$, $R_8$, $R_9$, and $R_{10}$ may be of straight chain or branched chain type, and examples thereof include ethynyloxy, (1- or 2-)propynyloxy, (1-, 2-, or 3-)butynyloxy, 1-methyldithyloxy, 1-methyl-1-propynyloxy, and 2-methyl-1-propynyloxy. The $C_{2-4}$ alkynyloxy is preferably straight chain $C_{2-4}$ alkynyloxy, and examples thereof include ethynyloxy, (1- or 2-)propynyloxy, and (1-, 2-, or 3-)butynyloxy.

$C_{2-4}$ alkynyloxy represented by $R_6$, $R_7$, $R_8$, $R_9$, and $R_{10}$ is optionally substituted by a halogen atom(s). Examples of $C_{2-4}$ alkynyloxy that is substituted by a halogen atom(s) and is represented by $R_6$, $R_7$, $R_8$, $R_9$, and $R_{10}$ include fluoroethynyloxy, chloroethynyloxy, and 3-chloro (1- or 2-)propynyloxy.

Examples of —O—$(CH_2)$n-O— wherein n is 1 or 2 and that is optionally substituted by one or more halogen atoms and is represented by combining any two adjacent substituents of $R_6$, $R_7$, $R_8$, $R_9$, and $R_{10}$ together include —O—

$(CF_2)_2$—O—, —O—$(CH_2)_2$—O—, —O—$CH_2CF_2$—O—, and —O—$CHFCF_2$—O—. Preferred is —O—$(CF_2)_2$—O—.

In a preferred embodiment of the present invention, $R_6$, $R_7$, $R_8$, $R_9$, and $R_{10}$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or alternatively, $R_7$ and $R_8$ together represent —O—$(CF_2)_2$—O—. In a more preferred embodiment, any one of $R_6$, $R_7$, $R_8$, $R_9$, and $R_{10}$ represents trifluoromethyl, methoxy, trifluoromethoxy, or 1,1,2,2-tetrafluoroethoxy with the other four substituents representing a hydrogen atom. Alternatively, $R_7$ and $R_8$ together represent —O—$(CF_2)_2$—O—.

$C_{1-8}$ alkyl represented by $R_{11}$, $R_{12}$, and $R_{13}$ may be of straight chain or branched chain type, and examples thereof include methyl, ethyl, propyl, i-propyl, n-butyl, i-butyl, s-butyl, t-butyl, n-pentyl, (2- or 3-methyl)butyl, 2,3-dimethylpropyl, n-hexyl, (2,3 or 4-methyl)pentyl, (2,3-, 2,4-, or 3,4-dimethyl)butyl, 2,3,4-trimethylpropyl, n-heptyl, and n-octyl.

$C_{1-8}$ alkyl represented by $R_{11}$, $R_{12}$, and $R_{13}$ is optionally substituted by a halogen atom(s). Examples of $C_{1-8}$ alkyl that is substituted by a halogen atom(s) and is represented by $R_{11}$, $R_{12}$, and $R_{13}$ include chloromethyl, trichloromethyl, trifluoromethyl, (1- or 2-)chloroethyl, 2,2,2-trifluoroethyl, 1,1,2,2-tetrafluoroethyl, and pentafluoroethyl.

$C_{1-8}$ alkyl represented by $R_{11}$, $R_{12}$, and $R_{13}$ is optionally substituted by $C_{1-4}$ alkoxy optionally substituted by a halogen atom(s). Examples of $C_{1-8}$ alkyl that is substituted by $C_{1-4}$ alkoxy optionally substituted by a halogen atom(s) and is represented by $R_{11}$, $R_{12}$, and $R_{13}$ include 2-trifluoromethoxyethyl.

Specific examples of $C_{3-6}$ cyclic alkyl that is optionally substituted by a halogen atom(s) and is represented by $R_{11}$, $R_{12}$, and $R_{13}$ include cyclopropylmethyl, cyclopropylethyl, cyclopropylpropyl, 1-methylcyclopropylmethyl, 2-(1-methylcyclopropyl)ethyl, 2,2-dimethylcyclopropylmethyl, 2,2-dichlorocyclopropylmethyl, 2-(2,2-dichlorocyclopropyl)ethyl, 3-(2,2-dichlorocyclopropyl)propyl, 2,2-difluorocyclopropylmethyl, 2-(2,2-difluorocyclopropyl)ethyl, 3-(2,2-difluorocyclopropyl)propyl, and cyclohexyl.

$C_{2-4}$ alkenyl represented by $R_{11}$, $R_{12}$, and $R_{13}$ may be of straight chain or branched chain type, and examples thereof include vinyl, (1- or 2-)propenyl, (1-, 2-, or 3-)butenyl, 1-methylvinyl, 1-methyl-1-propenyl, and 2-methyl-1-propenyl. The $C_{2-4}$ alkenyl is preferably straight chain $C_{2-4}$ alkenyl, and examples thereof include vinyl, (1- or 2-)propenyl, and (1-, 2-, or 3-)butenyl.

$C_{2-4}$ alkenyl represented by $R_{11}$, $R_{12}$, and $R_{13}$ is optionally substituted by a halogen atom(s). Examples of $C_{2-4}$ alkenyl that is substituted by a halogen atom(s) and is represented by $R_{11}$, $R_{12}$, and $R_{13}$ include 2-fluorovinyl, 2-chlorovinyl, 2,2-difluorovinyl, and 2,2-dichlorovinyl.

$C_{2-4}$ alkenyl represented by $R_{11}$, $R_{12}$, and $R_{13}$ is optionally substituted by $C_{1-4}$ alkoxy optionally substituted by a halogen atom(s). Examples of $C_{2-4}$ alkenyl that is substituted by $C_{1-4}$ alkoxy optionally substituted by a halogen atom(s) and is represented by $R_{11}$, $R_{12}$, and $R_{13}$ include 2-trifluoromethoxyvinyl.

In a preferred embodiment of the present invention, $R_{11}$ represents $C_{1-4}$ alkyl optionally substituted by a halogen atom(s); or $OR_{12}$ wherein $R_{12}$ represents $C_{1-4}$ alkyl optionally substituted by a halogen atom(s). In a more preferred embodiment, $R_{11}$ represents $OR_{12}$ wherein $R_{12}$ represents $C_{1-4}$ alkyl. The $C_{1-4}$ alkyl in these embodiments is preferably straight chain $C_{1-4}$ alkyl, more preferably methyl.

In a preferred embodiment in connection with a combination of substituents $R_1$ to $R_{11}$, $R_1$, $R_2$, and $R_3$ each independently represent a hydrogen atom, a chlorine atom, a bromine atom, a fluorine atom, methyl, ethyl, methoxy, ethoxy, or trifluoromethyl, provided that $R_1$, $R_2$, and $R_3$ do not simultaneously represent a hydrogen atom; $R_4$ and $R_5$ each independently represent a hydrogen atom, or $C_{1-4}$ alkyl optionally substituted by a halogen atom(s), provided that $R_4$ and $R_5$ do not simultaneously represent a hydrogen atom; $R_6$, $R_7$, $R_8$, $R_9$, and $R_{10}$ each independently represent a hydrogen atom, a chlorine atom, a bromine atom, a fluorine atom, methyl, ethyl, methoxy, ethoxy, trifluoromethyl, pentafluoroethyl, trifluoromethoxy, or 1,1,2,2-tetrafluoroethoxy, or alternatively, $R_7$ and $R_8$ together represent —O—$(CF_2)_2$—O—; $R_{11}$ represents $C_{1-4}$ alkyl optionally substituted by a halogen atom(s), or $OR_{12}$ wherein $R_{12}$ represents $C_{1-4}$ alkyl optionally substituted by a halogen atom(s).

In a more preferred embodiment, any one of $R_1$, $R_2$, and $R_3$ represents methyl, trifluoromethyl, or methoxy with the other two substituents representing a hydrogen atom; $R_4$ and $R_5$ each independently represent $C_{1-4}$ alkyl optionally substituted by a halogen atom(s); and any one of $R_6$, $R_7$, $R_8$, $R_9$, and $R_{10}$ represents trifluoromethyl, methoxy, trifluoromethoxy, or 1,1,2,2-tetrafluoroethoxy with the other four substituents representing a hydrogen atom, or alternatively, $R_7$ and $R_8$ together represent —O—$(CF_2)_2$—O—; and $R_{11}$ represents $OR_{12}$ wherein $R_{12}$ represents $C_{1-4}$ alkyl.

In a particularly preferred embodiment, any one of $R_1$ and $R_2$ represents methyl, trifluoromethyl, or methoxy with the other substituent representing a hydrogen atom; $R_3$ represents a hydrogen atom; $R_4$ represents methyl, ethyl, n-propyl, or butyl; $R_5$ represents methyl, ethyl, propyl, or butyl; and any one of $R_6$, $R_7$, $R_8$, $R_9$, and $R_{10}$ represents trifluoromethyl, methoxy, trifluoromethoxy, or 1,1,2,2-tetrafluoroethoxy with the other four substituents representing a hydrogen atom, or alternatively, $R_7$ and $R_8$ together represent —O—$(CF_2)_2$—O; and $R_{11}$ represents $OR_{12}$ wherein $R_{12}$ represents $C_{1-4}$ alkyl.

According to the process of the present invention, 4-carbonyloxyquinoline derivatives that are represented by general formula (1) and are useful as agricultural and horticultural insecticides or agricultural and horticultural fungicides can be obtained by condensing a quinolone derivative represented by general formula (2) with a halogenated compound represented by general formula (3) or an acid anhydride represented by general formula (4) in the presence of a phase transfer catalyst and a base. The present invention will be described in more detail.

The production process according to the present invention includes reacting a quinolone derivative represented by general formula (2) with a halogenated compound represented by general formula (3) or an acid anhydride represented by general formula (4) to give a 4-carbonyloxyquinoline derivative represented by general formula (1).

Specific examples of halogenated compounds represented by general formula (3) include acetic acid halide, propionic acid halide, butanoic acid halide, cyclopropylcarboxylic acid halide, cyclopentylcarboxylic acid halide, cyclohexylcarboxylic acid halide, n-hexanoic acid halide, n-octanoic acid halide, n-nonanoic acid halide, 2,2-dimethyipropanoic acid halide, acrylic acid halide, methacrylic acid halide, crotonic acid halide, isocrotonic acid halide, methyl formate halide, ethyl formate halide, isopropyl formate halide, butyl formate halide, and octyl formate halide. Halides and halogenated products are preferably chlorides and bromides. Chlorides are particularly preferred from the viewpoints of easiness on the preparation and availability of starting compounds.

Specific examples of acid anhydrides represented by general formula (4) include acetic anhydride, chloroacetic anhydride, trifluoroacetic anhydride, cyclohexanecarboxylic acid anhydride. Acetic anhydride is more preferred.

The production process according to the present invention is carried out in the presence of a phase transfer catalyst. Examples of phase transfer catalysts usable herein include quaternary ammonium salts such as tetraethyl ammonium chloride, tetraethylammonium bromide, tetrabutylammonium hydroxide, tetrabutylammonium bromide, benzyltribuylammonium chloride, and methyltrioctylammonium chloride; quaternary phosphonium salts such as tetraethylphosphonium chloride, tetraethylphosphonium bromide, and tetrabutylphosphonium bromide; and crown ethers such as 15-crown-5 and 18-crown-6. The phase transfer catalyst should be properly optimally selected in combination with a base that is used simultaneously therewith and will be described later. When metal carboxides, metal hydroxides, metal alkoxides, and metal hydrides are used as the base, the phase transfer catalyst is preferably a quaternally ammonium salt, more preferably tetrabutylammonium bromide.

The amount of the phase transfer catalyst used is not particularly limited but is preferably 0.01 to 0.1 time by mole, more preferably 0.03 to 0.06 time by mole, for the amount of the quinolone derivative.

The production process according to the present invention is carried out in the presence of a base. Examples of bases usable herein include inorganic bases such as carboxides of alkali metals or alkaline earth metals or hydroxides of alkali metals or alkaline earth metals; alkoxides of alkali metals or alkaline earth metals; and metal hydrides of alkali metals or alkaline earth metals. Preferred is potassium carbonate, sodium carbonate, calcium carbonate, sodium hydrogencarbonate, sodium hydroxide, sodium methoxide, sodium ethoxide, sodium-t-butoxide, or sodium hydride. Inorganic bases such as carboxides or hydroxides of alkali metals or alkaline earth metals are less hazardous, easy to handle, easily available, and inexpensive and thus are advantageous in industrial production. From this standpoint, the base used is preferably sodium carbonate, potassium carbonate, sodium hydroxide, or potassium hydroxide, and is particularly preferably sodium hydroxide.

The base may be used in any form of solids or solutions using suitable solvents in a reaction in the production process according to the present invention. When the base is used as a solid in the reaction, the base is preferably ground into fine particles before use. When the base is used as a solution in the reaction, the base is dissolved in a soluble solvent inert to the base before use. Preferably, the base solution is prepared as a high-concentration solution which is then used in the reaction. Specifically, the solution of the base used preferably has a concentration of 8 to 14N, more preferably has a concentration of 30 to 70% by weight, still more preferably has a concentration of 40 to 60% by weight. Particularly preferably, the base is in the form of an 8 to 14N aqueous sodium hydroxide or potassium hydroxide solution or aqueous sodium carbonate or potassium carbonate solution.

The amount of the base used is preferably 0.1 to 5.0 times by mole, more preferably 0.5 to 3.0 times by mole, for the amount of the quinolone derivative.

The production process according to the present invention can be typically carried out in the presence of a solvent. Any solvent that does not hinder the reaction may be used without particular limitation. These solvents may be used as a single solvent or as a mixed solvent composed of two or more of them. Mixed solvents are more preferred. The mixed solvent is preferably composed of water and an organic solvent. Solvents usable in the production process according to the present invention include water, aromatic hydrocarbons such as benzene, toluene, xylene, and mesitylene; halogenated aromatic hydrocarbons such as chlorobenzene and dichlorobenzene; halogenated aliphatic hydrocarbons such as methylene chloride, chloroform, and dichloroethane; aliphatic hydrocarbons such as peptane, hexane, heptane, 2-methylbutane, 2-methylpentane, 2-methylhexane, cyclopentane, cyclohexane, and cycloheptane; amides such as dimethylformamide, dimethyl acetamide, and N-methylpyrrolidone; ethers such as diisopyl ether; and ketones such as 2-butanone.

The aromatic hydrocarbons, the halogenated aromatic hydrocarbons, the halogenated aliphatic hydrocarbons, the aliphatic hydrocarbons, the amide, and ethers function as a reaction solvent for dissolution of the quinolone derivatives and the halogenated compounds or the acid anhydrides. Among these solvents, the aromatic hydrocarbons and the halogenated aliphatic hydrocarbons are easily available, inexpensive, and can be relatively easily removed by evaporation and thus are industrially advantageous. Thus, these solvents are preferably used as main reaction solvents in the production process according to the present invention. Specifically, toluene, xylene, and methylene chloride are particularly preferred. The solvent is more preferably a mixed solvent composed of the aromatic hydrocarbons, aliphatic hydrocarbons, or halogenated aliphatic hydrocarbons and a small amount of the amides added to these solvents as a cosolvent. These mixed solvents can enhance the solubility of the quinolone derivative and can realize a reduction in necessary amount of the solvent. Particularly preferred are mixed solvents composed of the aromatic hydrocarbons and the amides or mixed solvents composed of the halogenated aliphatic hydrocarbons and the amides. In the mixed solvents, the mixing ratio is such that the amount of the aromatic hydrocarbons or the halogenated aliphatic hydrocarbons is 3 to 20 parts by mass based on one part by mass of the amides.

The amount of the solvent used is preferably 2 to 50 times by mass, more preferably 3 to 30 times by mass, for the amount of the quinolone derivative.

On the other hand, water when added to the solvent functions as a solvent for dissolution of the base. Water may be added separately, or alternatively may be added as an aqueous base solution. Water may be used in an amount that can dissolve the base added, specifically in an amount of 0.01 to 0.1 time by mass, for the amount of the solvent for dissolution of the quinolone derivative.

In the production process according to the present invention, aromatic hydrocarbons-amides-water solvents are particularly preferred solvents. In another embodiment, halogenated aliphatic hydrocarbons-amides-water solvents are used.

In the production process according to the present invention, preferably, the quinolone derivative and the halogenated compound are brought into contact with each other in a liquid phase in the presence of a phase transfer catalyst and a base. For example, a condensation reaction is carried out under ordinary pressure, applied pressure, or reduced pressure by a method the includes mixing a quinolone derivative, a phase transfer catalyst, a base, a halogenated compound, and a solvent together while stirring under an inert gas atmosphere. The reaction temperature at that time is preferably −50 to 100° C., more preferably −10 to 50° C. The quinolone derivative may be used in the form of a salt with the base.

After the completion of the reaction, the 4-carbonyloxyquinoline derivative that is a contemplated product according to the present invention can be isolated by simple general post treatment such as extraction or precipitation. As described above, in the production process according to the present invention, suitable conditions are such that mixed solvents composed of main reaction solvents of aromatic hydrocarbons or halogenated aliphatic hydrocarbons, specifically toluene, xylene, or methylene chloride, and a small amount of amide solvents, specifically dimethylformamide, dimethyl acetamide, or N-methylpyrrolidone as a cosolvent added to the main reaction solvent for dissolution aiding purposes are used as the solvent. In this case, the 4-carbonyloxyquinoline derivative as the contemplated product can be precipitated and isolated by a simple procedure, that is, removing the main solvent by evaporation. Alternatively, the contemplated product can be precipitated and isolated by removing the main solvent by evaporation and then adding a small amount of a solvent in which the contemplated product is insoluble or sparingly soluble. In the later method, the solvent added for precipitating the contemplated product is not particularly limited but is preferably water. In the production process according to the present invention, solvents that can easily be removed by evaporation can be used as the main reaction solvent. Accordingly, the production process according to the present invention is industrially advantageous in that the contemplated product can be isolated by a simple procedure and the volume of a product precipitation tank can be reduced.

The 4-carbonyloxyquinoline derivative that has been produced by the production process according to the present invention and then isolated is obtained as an isolated product having a high purity at a high yield by recovering the precipitated solid by filtration. If necessary, the 4-carbonyloxyquinoline derivative may be separated and purified by recrystallization for use as agricultural chemicals.

Specific examples of 4-carbonyloxyquinoline derivatives that are obtained by the process of the present invention and are represented by general formula (1) are shown in Table 1 below. These quinoline derivatives are useful as agricultural chemicals.

[Chemical formula 5]

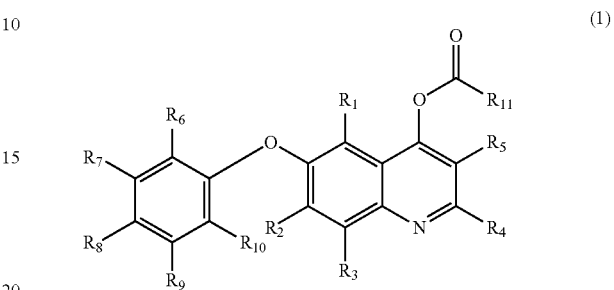

(1)

TABLE 1

| Compound No. | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 1 | H | Me | H | Et | Me | H | H | $OCF_3$ | H | H | OMe |
| 2 | Me | Me | H | Et | Me | H | H | $OCF_3$ | H | H | OMe |
| 3 | H | Me | H | Et | Me | H | H | $OCF_2CHF_2$ | H | H | OMe |
| 4 | H | Me | H | Et | Me | H | —$OCF_2CHF_2O$— | | H | H | OMe |
| 5 | H | Me | H | Et | Me | Cl | H | $OCF_3$ | H | H | OMe |
| 6 | H | OMe | H | Et | Me | H | H | $OCF_2CHF_2$ | H | H | OMe |
| 7 | H | OMe | H | Et | Me | H | —$OCF_2CHF_2O$— | | H | H | OMe |
| 8 | H | F | H | Me | Me | H | H | $OCF_3$ | H | H | OMe |
| 9 | Cl | H | H | Me | Me | H | H | Cl | H | H | Me |
| 10 | H | Cl | H | Me | Me | H | H | Cl | H | H | Me |
| 11 | $CF_3$ | H | H | Me | Me | H | H | $OCF_3$ | H | H | Me |
| 12 | H | $CF_3$ | H | Me | Me | H | H | $OCF_3$ | H | H | Me |
| 13 | $CF_3$ | H | H | Me | Me | H | H | $CF_3$ | H | Cl | Me |
| 14 | H | $CF_3$ | H | Me | Me | H | H | $CF_3$ | H | Cl | Me |
| 15 | CF | H | H | Et | Me | H | H | $OCF_3$ | H | H | OMe |
| 16 | H | $CF_3$ | H | Et | Me | H | H | $OCF_3$ | H | H | OMe |
| 17 | $CF_3$ | H | H | Me | Me | H | H | $CF_3$ | H | Cl | Me |
| 18 | H | $CF_3$ | H | Me | Me | H | H | $OCF_3$ | H | Cl | Me |
| 19 | Cl | H | H | Me | Me | H | H | OMe | H | H | Me |
| 20 | H | Cl | H | Me | Me | H | H | OMe | H | H | Me |
| 21 | Me | H | H | Me | Me | H | H | $OCF_3$ | H | H | Me |
| 22 | H | Me | H | Me | Me | H | H | $OCF_3$ | H | H | Me |
| 23 | Me | Me | H | Me | Me | H | H | $OCF_2$ | H | H | Me |
| 24 | $CF_3$ | H | H | Me | Me | H | H | $OCF_3$ | H | H | cPr |
| 25 | H | Br | H | Me | Me | H | H | $OCF_3$ | H | H | Me |
| 26 | H | Br | H | Me | Me | H | H | $OCF_3$ | H | H | OMe |
| 27 | Me | Me | H | Et | Me | H | H | $OCH_2CH=CCl_2$ | H | H | OMe |
| 28 | Me | Me | H | Et | Me | H | H | $OCH_2C\equiv CCl$ | H | H | OMe |
| 29 | H | $CH_2OMe$ | H | Et | Me | H | H | $OCF_3$ | H | H | OMe |
| 30 | OMe | H | OMe | Et | Me | H | H | $OCF_3$ | H | H | OMe |
| 31 | H | F | H | Me | Me | H | H | $SCF(CF_3)_2$ | H | H | OMe |
| 32 | H | F | H | Me | Me | H | H | $SCF(CF_3)_2$ | H | H | Me |

In a preferred aspect of the present invention, there is provided a process for producing a 4-carbonyloxyquinoline derivative represented by general formula (1), the process comprising reacting a quinolone derivative represented by general formula (2) with a halogenated compound represented by general formula (3) or an acid anhydride represented by general formula (4) in the presence of a quaternary ammonium salt and a hydroxide of an alkali metal or an alkaline earth metal.

In another preferred aspect of the present invention, there is provided a process for producing a 4-carbonyloxyquinoline derivative represented by general formula (1), the process comprising reacting a quinolone derivative represented by general formula (2) with a halogenated compound represented by general formula (3) or an acid anhydride represented by general formula (4) in the presence of tetrabutylammonium bromide and a hydroxide of an alkali metal or an alkaline earth metal.

In still another preferred aspect of the present invention, there is provided a process for producing a 4-carbonyloxyquinoline derivative represented by general formula (1), the process comprising reacting a quinolone derivative represented by general formula (2) with a halogenated compound represented by general formula (3) or an acid anhydride represented by general formula (4) in the presence of a quaternary ammonium salt and sodium hydroxide.

In a further preferred aspect of the present invention, there is provided a process for producing a 4-carbonyloxyquinoline derivative represented by general formula (1), the process comprising reacting a quinolone derivative represented by general formula (2) with a halogenated compound represented by general formula (3) or an acid anhydride represented by general formula (4) in the presence of tetrabutylammonium bromide and sodium hydroxide.

EXAMPLES

The present invention is further illustrated by the following Examples that are not intended as a limitation of the invention.

Example 1

Synthesis of 2-ethyl-3,7-dimethyl-6-(4-(trifluoromethoxy)phenoxy)quinolin-4-yl methyl carbonate Toluene (810 ml), 90 ml of dimethyl acetamide, 113.2 g of 2-ethyl-3,7-dimethyl-6-(4-(trifluoromethoxy)phenoxy)quinolin-4(1H)-one, and 4.8 g of tetrabutylammonium bromide were added to a glass vessel equipped with a stirring device, a thermometer, and a reflux condenser and having a volume of 3000 ml, and the mixture was stirred at room temperature. A 48% aqueous sodium hydroxide solution (50 g) was added dropwise thereto at 30 to 35° C., and the mixture was stirred at the same temperature for one hr. After cooling to 10 to 15° C., 34 g of methyl chloroformate was added dropwise, and a reaction was allowed to proceed at the same temperature for one hr. Water was added to the reaction solution. After washing, toluene was removed by evaporation, and the precipitated solid was collected by a suction filter. The solid was dried in vacuo to give 2-ethyl-3,7-dimethyl-6-(4-(trifluoromethoxy)phenoxy)quinolin-4-yl methyl carbonate (128 g, yield 98%). It was confirmed from the results of measurement of $^1$H-NMR that the compound thus obtained was a compound of No. 120 described in WO2006/013896 (patent document 1).

$^1$H-NMR (CDCl$_3$): 1.38 (t, 3H), 2.31 (s, 3H), 2.41 (s, 3H), 3.01 (q, 2H), 3.88 (s, 3H), 6.97 (d, 2H), 7.14 (s, 1H), 7.20 (d, 2H), 7.94 (s, 1H).

Example 2

Synthesis of 2-ethyl-3,7-dimethyl-6-(4-(trifluoromethoxy)phenoxy)quinolin-4-yl methyl carbonate Methylene chloride (1000 ml), 160 ml of dimethyl acetamide, 113.2 g of 2-ethyl-3,7-dimethyl-6-(4-(trifluoromethoxy)phenoxy)quinolin-4(1H)-one, and 4.8 g of tetrabutylammonium bromide were added to a glass vessel equipped with a stirring device, a thermometer, and a reflux condenser and having a volume of 3000 ml, and the mixture was stirred at room temperature. A 48% aqueous sodium hydroxide solution (50 g) was added dropwise at 25 to 30° C., and the mixture was stirred at the same temperature for one hr. After cooling to 10 to 15° C., 34 g of methyl chloroformate was added dropwise, and a reaction was allowed to proceed at the same temperature for one hr. Water was added to the reaction solution for washing. Methylene chloride was removed by evaporation, 990 ml of methanol was added to the residue, and the mixture was heated to dissolve the residue in methanol. Water (660 ml) was added dropwise thereto to precipitate crystals, and the precipitated solid was collected by a suction filter. The solid was dried in vacuo to give 2-ethyl-3,7-dimethyl-6-(4-(trifluoromethoxy)phenoxy)quinolin-4-yl methyl carbonate (124.4 g, yield 95.2%). It was confirmed from the results of measurement of $^1$H-NMR that the compound thus obtained was a compound of No. 120 described in WO2006/013896 (patent document 1).

$^1$H-NMR (CDCl$_3$): 1.38 (t, 3H), 2.31 (s, 3H), 2.41 (s, 3H), 3.01 (q, 2H), 3.88 (s, 3H), 6.97 (d, 2H), 7.14 (s, 1H), 7.20 (d, 2H), 7.94 (s, 1H).

Comparative Example 1

Synthesis of 2-ethyl-3,7-dimethyl-6-(4-(trifluoromethoxy)phenoxy)quinolin-4-yl methyl carbonate Toluene (405 ml), 45 ml of dimethyl acetamide, and 56.6 g of 2-ethyl-3,7-dimethyl-6-(4-(trifluoromethoxy)phenoxy)quinolin-4(1H)-one were added to a glass vessel equipped with a stirring device, a thermometer, and a reflux condenser and having a volume of 2000 ml, and the mixture was stirred at room temperature. A 48% aqueous sodium hydroxide solution (25 g) was added dropwise at 30 to 35° C., and the mixture was stirred at the same temperature for one hr. After cooling to 10 to 15° C., 17 g of methyl chloroformate was added dropwise, and a reaction was allowed to proceed at the same temperature for one hr. Water was added to the reaction solution, and the precipitated solid was collected by filtration and was dried to recover the unreacted starting compound 2-ethyl-3,7-dimethyl-6-(4-(trifluoromethoxy)phenoxy)quinolin-4(1H)-one (6.5 g, yield 11.5%). The toluene layer of the filtrate was washed with water and was then concentrated to give 2-ethyl-3,7-dimethyl-6-(4-(trifluoromethoxy)phenoxy)quinolin-4-yl methyl carbonate (54.8 g, yield 83.9%).

Comparative Example 2

Synthesis of 2-ethyl-3,7-dimethyl-6-(4-(trifluoromethoxy)phenoxy)quinolin-4-yl methyl carbonate Sodium-t-butoxide (15.1 g), 45 ml of dimethyl acetamide, 405 ml of toluene, and 56.6 g of 2-ethyl-3,7-dimethyl-6-(4-(trifluoromethoxy)phenoxy)quinolin-4(1H)-one were added to a glass vessel equipped with a stirring device, a thermometer and a reflux condenser and having a volume of 2000 ml, and the mixture was stirred at 30 to 35° C. for one hr. After cooling to 10 to 15° C., 15 g of methyl chloroformate was added dropwise thereto, and a reaction was allowed to proceed at the same temperature for one hr. Water was added to the reaction solution, and the precipitated solid was collected by filtration and was dried to recover the unreacted starting compound 2-ethyl-3,7-dimethyl-6-(4-(trifluoromethoxy)phenoxy)quinolin-4(1H)-one (6.4 g, yield 11.3%). The toluene layer of the filtrate was washed with water and was concentrated to give 2-ethyl-3,7-dimethyl-6-(4-(trifluoromethoxy)phenoxy)quinolin-4-yl methyl carbonate (55.6 g, yield 85.1%).

Reference Example 1

WO2010/007964 (Patent Document 4)

Example 6

Synthesis of 2-ethyl-3,7-dimethyl-6-(4-(trifluoromethoxy)phenoxy)quinolin-4-yl methyl carbonate Dimethyl acetamide (694 ml), 35.2 g of sodium-t-butoxide, and 131 g of 2-ethyl-3,7-dimethyl-6-(4-(trifluoromethoxy)phenoxy)quinolin-4(1H)-one were added to a glass vessel equipped with a stirring device, a thermometer, and a reflux condenser and having a volume of 1000 ml under a nitrogen atmosphere, and the mixture was stirred at room temperature. Methyl chloroformate (34.4 g) was added dropwise thereto, and a reaction was allowed to proceed at room temperature for one hr. The reaction mixture was poured into 1735 ml of water contained in a 5-L plastic vessel, and the mixture was stirred at room temperature for 2 hr. The precipitated solid was collected by a suction filter and was washed with water. The solid was dried in vacuo to give 2-ethyl-3,7-dimethyl-6-(4-(trifluoromethoxy)phenoxy)quinolin-4-yl methyl carbonate (149.5 g, yield 98.8%).

Reference Example 2

WO2010/007964 (Patent Document 4)

Example 8

Synthesis of 2-ethyl-3,7-dimethyl-6-(4-(trifluoromethoxy)phenoxy)quinolin-4-yl methyl carbonate Dimethyl acetamide (980 ml) and 98 g of 2-ethyl-3,7-dimethyl-6-(4-(trifluoromethoxy)phenoxy)quinolin-4(1H)-one were charged into a glass flask equipped with a stirring device, a thermometer, a reflux condenser, and a calcium chloride tube and having a volume of 2000 ml under a nitrogen atmosphere, and the mixture was cooled to 15° C. 55% sodium hydride (18.2 g) was added thereto, and the mixture was stirred at 15 to 20° C. for one hr. Methyl chloroformate (32.1 g) was added dropwise, and a reaction was allowed to proceed at room temperature for one hr. The reaction mixture was poured into 5 L of ice water contained in a 10-L plastic container, and the mixture was stirred at room temperature for 2 hr. The precipitated solid was collected by a suction filter and was washed with n-hexane and water. The solid was dried in vacuo to give 2-ethyl-3,7-dimethyl-6-(4-(trifluoromethoxy)phenoxy)quinolin-4-yl methyl carbonate (103.3 g, yield 91.4%).

Effect of the Invention

In a conventional process for producing 4-carbonyloxyquinoline derivatives of Reference Examples 1 and 2 (WO2010/007964 (patent document 4), Examples 6 and 8), sodium-t-butoxide or sodium hydride is used as the base. These bases are highly reactive and, when added in an excessive amount, leads to decomposition of the contemplated product. Accordingly, the amount of the base to be charged should be closely regulated. Further, these bases are hygroscopically decomposable and thus are difficult to handle. Further, since these bases are expensive, the process has room for further improvement as a production process on a commercial scale. Furthermore, since a large amount of dimethyl acetamide should be used as a reaction solvent, water in an amount of 2.5 to 5.1 times by volume for the amount of dimethyl acetamide charged should be added in the isolation of the product. This requirement leads to a necessity of increasing the volume of the crystallization tank and, at the same time, leads to a possibility of a lowering in operation efficiency in the recovery of the precipitated solid through filtration. Furthermore, the content of dimethyl acetamide in the filtrate is so large that a load on waste water is large and, thus, dimethyl acetamide that is a high-boiling solvent should be sometimes recovered from waste water.

In the process for producing 4-carbonyloxyquinoline derivatives according to the present invention, the use of the phase transfer catalyst has made it possible to use bases that are inexpensive and easy to handle, such as sodium hydroxide. The process according to the present invention is also advantageous in that, even when an excessive base equivalent is used in the reaction, the contemplated product is hardly decomposed and there is no need to closely regulate the equivalent of the base charged.

Further, the process according to the present invention is also advantageous in that reaction solvents that are easily removable by evaporation, such as toluene and methylene chloride, can be applied. Specifically, after the completion of the reaction, the contemplated product can be crystallized in a small-volume crystallization tank by performing simple aqueous washing as post treatment and then removing the solvent by evaporation, and this offers a significant effect in an isolation and purification efficiency. Furthermore, the amount of dimethyl acetamide used is so small that a load on waste water is also reduced and, thus, the process according to the present invention is industrially advantageous.

Specifically, the above Examples have demonstrated that, in the process for producing 4-carbonyloxyquinoline derivatives according to the present invention, the use of a phase transfer catalyst in a reaction between a quinolone derivative and a halogenated compound or an acid anhydride makes it possible to use inexpensive and easy-to-handle bases and, by virtue of this, the process according to the present invention has no need to closely regulate the equivalent of the base charged and can use reaction solvents easily removable by evaporation, and can reduce a load on waste water, that is, is industrially advantageous, and, at the same time, can realize a high yield.

The invention claimed is:
1. A process for producing a 4-carbonyloxyquinoline derivative represented by general formula (1):

[Chemical formula 1]

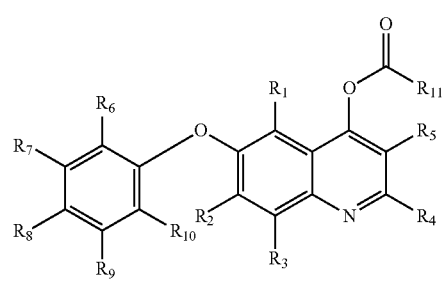

wherein
$R_1$, $R_2$, and $R_3$ each independently represent a hydrogen atom, a halogen atom, $C_{1-4}$ alkyl optionally substituted by a halogen atom(s), or $C_{1-4}$ alkoxy optionally substituted by a halogen atom(s), provided that $R_1$, $R_2$, and $R_3$ do not simultaneously represent a hydrogen atom, $R_4$ and $R_5$ each independently represent a hydrogen atom or $C_{1-4}$ alkyl optionally substituted by a halogen atom(s), provided that $R_4$ and $R_5$ do not simultaneously represent a hydrogen atom, or $R_4$ and $R_5$ together represent —$(CH_2)$m- wherein m is 3 or 4, and $R_6$, $R_7$, $R_8$, $R_9$, and $R_{10}$ each independently represent a hydrogen atom, a halogen atom, $C_{1-8}$ alkyl optionally substituted by a halogen atom(s), $C_{1-8}$ alkoxy optionally substituted by a halogen atom(s), $C_{1-8}$ alkylthio optionally substituted by a halogen atom(s), $C_{2-4}$ alkenyloxy optionally substituted by a halogen atom(s), $C_{2-4}$ alkenylthio optionally substituted by a halogen atom(s), or $C_{2-4}$ alkynyloxy optionally substituted by a halogen atom(s), or any two adjacent substituents of $R_6$, $R_7$, $R_8$, $R_9$, and $R_{10}$ together represent —O—$(CH_2)$n-O— optionally substituted by one or more halogen atoms, wherein n is 1 or 2, and $R_{11}$ represents $C_{1-8}$ alkyl optionally substituted by a halogen atom(s); $C_{3-6}$ cyclic alkyl optionally substituted by a halogen atom(s); $C_{2-4}$ alkenyl optionally substituted by a halogen atom(s); $OR_{12}$ wherein $R_{12}$ represents $C_{1-8}$ alkyl optionally substituted by a halogen atom(s), $C_{3-6}$ cyclic alkyl optionally substituted by a halogen atom(s), or $C_{2-4}$ alkenyl optionally substituted by a halogen atom(s); $SR_{13}$ wherein $R_{13}$ represents $C_{1-8}$ alkyl optionally substituted by a halogen atom(s), $C_{3-6}$ cyclic alkyl optionally substituted by a halogen atom(s), or $C_{2-4}$ alkenyl optionally substituted by a halogen atom(s), the process comprising reacting a quinolone derivative represented by general formula (2):

[Chemical formula 2]

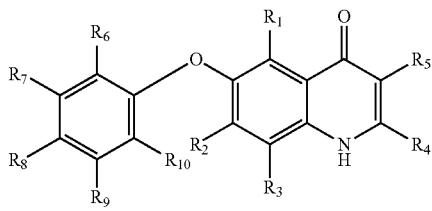

(2)

wherein $R_1$, $R_2$, $R_3$, $R_4$, $R_5$, $R_6$, $R_7$, $R_8$, $R_9$, and $R_{10}$ are as defined in formula (1), with a halogenated compound represented by general formula (3):

[Chemical formula 3]

$$R_{11}COX \quad (3)$$

wherein $R_{11}$ is as defined in formula (1); and X represents any one of fluorine, chlorine, bromine, and iodine, or an acid anhydride represented by general formula (4):

[Chemical formula 4]

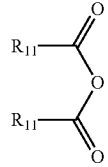

(4)

wherein $R_{11}$ is as defined in formula (1), in the presence of a phase transfer catalyst and a base, wherein the phase transfer catalyst is tetrabutylammonium bromide wherein the base is an aqueous hydroxide solution of an alkali metal or an alkaline earth metal or an aqueous carboxide solution of an alkali metal or an alkaline earth metal, and the base has a concentration of 40% or more by weight, wherein the solvent is a mixed solvent comprising amides and one solvent selected from the group consisting of aromatic hydrocarbons, halogenated aromatic hydrocarbons, halogenated aliphatic hydrocarbons, aliphatic hydrocarbons, ethers and ketones.

2. The process according to claim 1, wherein any one of $R_1$, $R_2$, and $R_3$ represents methyl, trifluoromethyl, or methoxy with the other two substituents representing a hydrogen atom; $R_4$ and $R_5$ each independently represent $C_{1-4}$ alkyl optionally substituted by a halogen atom(s); any one of $R_6$, $R_7$, $R_8$, $R_9$, and $R_{10}$ represents trifluoromethyl, methoxy, trifluoromethoxy, or 1,1,2,2-tetrafluoroethoxy with the other four substituents representing a hydrogen atom, or $R_7$ and $R_8$ together represent —O—$(CF_2)_2$—O—; and $R_{11}$ represents $OR_{12}$ wherein $R_{12}$ represents $C_{1-4}$ alkyl.

3. The process according to claim 1, wherein the base is an aqueous sodium hydroxide solution which has a concentration of 40% or more by weight.

4. The process according to claim 1, wherein the solvent is a mixed solvent comprising toluene and dimethyl acetamide.

* * * * *